United States Patent
Park et al.

(10) Patent No.: US 10,849,512 B2
(45) Date of Patent: Dec. 1, 2020

(54) DEVICES SYSTEMS AND METHODS FOR ASSESSING A VESSEL

(71) Applicant: KONINKLIJKE PHILIPS N.V., Eindhoven (NL)

(72) Inventors: Jinhyoung Park, Rancho Cordova, CA (US); Fergus Merritt, Rancho Cordova, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 254 days.

(21) Appl. No.: 15/745,651

(22) PCT Filed: Jul. 15, 2016

(86) PCT No.: PCT/EP2016/066917
§ 371 (c)(1),
(2) Date: Jan. 17, 2018

(87) PCT Pub. No.: WO2017/013020
PCT Pub. Date: Jan. 26, 2017

(65) Prior Publication Data
US 2018/0228387 A1 Aug. 16, 2018

Related U.S. Application Data

(60) Provisional application No. 62/194,066, filed on Jul. 17, 2015.

(51) Int. Cl.
*A61B 5/0215* (2006.01)
*A61B 5/00* (2006.01)
(Continued)

(52) U.S. Cl.
CPC ...... *A61B 5/02158* (2013.01); *A61B 5/02007* (2013.01); *A61B 5/6851* (2013.01);
(Continued)

(58) Field of Classification Search
None
See application file for complete search history.

(56) References Cited

U.S. PATENT DOCUMENTS 5,113,868 A   5/1992 Wise
5,178,153 A   1/1993 Enizig
(Continued)

FOREIGN PATENT DOCUMENTS

WO   2001013779 A2   3/2001

OTHER PUBLICATIONS

Development and Validation of a Novel Method to Derive Central Aortic Systolic Pressure From the Radial Pressure Waveform Using an N-Point Moving Average Method Bryan Williams, Peter S. Lacy, Peter Yan, Chua-Ngak Hwee, Chen Liang, Choon-Meng Ting J Am Coll Cardiol. Feb. 2011, 57 (8) 951-961. (Year: 2011).*
(Continued)

*Primary Examiner* — Patrick Fernandes
*Assistant Examiner* — Benjamin S Melhus

(57) ABSTRACT

An intravascular system includes at least one pressure-sensing instrument sized and shaped for introduction into a vessel of a patient; a processing unit in communication with the pressure-sensing instrument, the processing unit configured to: obtain proximal pressure measurements for at least one cardiac cycle of the patient while the pressure-sensing instrument is positioned proximal of a stenosis of the vessel; obtain distal pressure measurements while the pressure-sensing instrument is positioned distal of the stenosis; select a diagnostic window within a cardiac cycle by identifying a change in sign of a slope associated with the proximal and/or distal pressure measurements, wherein the diagnostic window encompasses only a portion of the cardiac cycle of the patient; calculate a pressure ratio between the distal and proximal obtained during the diagnostic window; and output the calculated pressure ratio to a display device in communication with the processing unit.

18 Claims, 14 Drawing Sheets

(51) Int. Cl.
*A61B 5/02* (2006.01)
*A61B 5/0456* (2006.01)
(52) U.S. Cl.
CPC .......... *A61B 5/6852* (2013.01); *A61B 5/7239* (2013.01); *A61B 5/0456* (2013.01)

(56) References Cited

U.S. PATENT DOCUMENTS

| | | | |
|---|---|---|---|
| 5,715,827 A | 2/1998 | Coir | |
| 5,807,265 A | 9/1998 | Itoigawa | |
| 6,193,669 B1* | 2/2001 | Degany | A61B 5/02014 600/486 |
| 9,339,348 B2 | 5/2016 | Davies et al. | |
| 2011/0178383 A1* | 7/2011 | Kassab | A61B 5/026 600/381 |
| 2014/0094697 A1* | 4/2014 | Petroff | A61B 1/07 600/427 |
| 2014/0135633 A1 | 5/2014 | Anderson | |
| 2016/0058307 A1* | 3/2016 | Svanerudh | A61B 5/7278 600/427 |

OTHER PUBLICATIONS

Jon E. Jenkins, Hemodynamics is a 12-letter word! An intro to the basics. Cath Lab Digest; vol. 15, No. 5; May 1, 2007.

\* cited by examiner

DEVICES SYSTEMS AND METHODS FOR ASSESSING A VESSEL

CROSS-REFERENCE TO PRIOR APPLICATIONS

This application is the U.S. National Phase application under 35 U.S.C. § 371 of International Application No. PCT/EP2016/066917, filed on Jul. 15, 2016, which claims the benefit of U.S. Provisional Patent Application No. 62/194,066, filed on Jul. 17, 2015. These applications are hereby incorporated by reference herein.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents.

SUMMARY

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries without the administration of a hyperemic agent. A subset of intravascular pressure measurements obtained during a diagnostic window can be used to calculate a pressure ratio. The diagnostic window can be determined without utilizing electrocardiogram (ECG) data, in some instances. Rather, in such instances, the intravascular pressure measurements can be divided into different time periods, and slopes respectively associated with each time period can be used to identify one or more features of the intravascular pressure measurements, a cardiac cycle of the patient, and/or the diagnostic window.

In some instances, an intravascular system is provided. The system includes at least one pressure-sensing instrument sized and shaped for introduction into a vessel of a patient; a processing unit in communication with the at least one pressure-sensing instrument, the processing unit configured to: obtain proximal pressure measurements for at least one cardiac cycle of the patient from the at least one pressure-sensing instrument while the at least one pressure-sensing instrument is positioned within the vessel at a position proximal of a stenosis of the vessel; obtain distal pressure measurements for the at least one cardiac cycle of the patient from the at least one pressure-sensing instrument while the at least one pressure-sensing instrument is positioned within the vessel at a position distal of the stenosis of the vessel; select a diagnostic window within a cardiac cycle of the patient by identifying a change in sign of a slope associated with at least one of the proximal pressure measurements or the distal pressure measurements, wherein the diagnostic window encompasses only a portion of the cardiac cycle of the patient; calculate a pressure ratio between the distal pressure measurements obtained during the diagnostic window and the proximal pressure measurements obtained during the diagnostic window; and output the calculated pressure ratio to a display device in communication with the processing unit.

In some embodiments, the processing unit is configured to select a diagnostic window without using electrocardiogram (ECG) data. In some embodiments, the proximal and distal pressure measurements are obtained without administration of a hyperemic agent. In some embodiments, the processing circuit is further configured to calculate the slope over multiple time periods within the cardiac cycle. In some embodiments, a single time period encompasses only a portion of the cardiac cycle. In some embodiments, time periods within the cardiac cycle have the same duration. In some embodiments, the processing circuit is further configured to calculate the slope over multiple time periods of a further cardiac cycle, wherein the time periods of the further cardiac cycle have a different duration than the time periods of the cardiac cycle. In some embodiments, a duration of the time periods is based on a duration of a cardiac cycle. In some embodiments, a duration of the time periods is based on a duration of time periods in one or more previous cardiac cycles. In some embodiments, consecutive time periods at least partially overlap in time. In some embodiments, a starting point of consecutive time periods are offset based on an acquisition rate of the at least one pressure-sensing instrument.

In some embodiments, the processing unit is further configured to identify a sign change of the slope based on calculation of the slope over the plurality of time periods. In some embodiments, the processing unit is further configured to determine, based on the sign change of the slope, at least one of: a minimum pressure measurement, a peak pressure measurement, a beginning of the cardiac cycle, an ending of the cardiac cycle, a beginning of systole, an ending of diastole, a starting point of the diagnostic window, or an ending point of the diagnostic window. In some embodiments, the processing unit is further configured to determine a starting point of the diagnostic window based on the sign change of the slope. In some embodiments, the starting point of the diagnostic window is offset from the sign change of the slope. In some embodiments, the processing unit is further configured to determine a peak pressure measurement based on the sign change of the slope. In some embodiments, the peak pressure measurement is offset from the sign change of the slope. In some embodiments, the processing unit is further configured to determine a starting point of the diagnostic window based on the peak pressure measurement. In some embodiments, the starting point of the diagnostic window is offset from the peak pressure measurement. In some embodiments, the processing unit is further configured to determine a maximum negative slope occurring after the peak pressure measurement. In some embodiments, the processing unit is further configured to determine a starting point of the diagnostic window based on the maximum negative slope. In some embodiments, the starting point of the diagnostic window is offset from the maximum negative slope. In some embodiments, the processing unit is further configured to determine a further sign change of the slope. In some embodiments, the processing unit is further configured to determine a minimum pressure measurement based on the further sign change of the slope. In some embodiments, the minimum pressure measurement is offset from the further sign change of the slope. In some embodiments, the processing unit is further configured to determine an ending point of the diagnostic window based on the minimum pressure measurement. In some embodiments, the ending point of the diagnostic window is offset from the minimum pressure measurement.

In some embodiments, the at least one pressure-sensing instrument comprises: a first pressure-sensing instrument sized and shaped to obtain the proximal pressure measurements while positioned within the vessel at a position proximal of the stenosis of the vessel; and a second pressure-sensing instrument sized and shaped to obtain the distal pressure measurements while positioned within the vessel at a position distal of the stenosis of the vessel. In some embodiments, at least one of the first or second pressure-sensing instruments comprises a catheter, a guide wire, or a guide catheter. In some embodiments, the first pressure-sensing instrument is a catheter and the second pressure-sensing instrument is a guide wire.

In some instances, a method of evaluating a vessel of a patient is provided. The method includes receiving, at a processing unit in communication with at least one pressure-sensing instrument sized and shaped for introduction into a vessel of the patient, proximal pressure measurements for at least one cardiac cycle of the patient while the at least one pressure-sensing instrument is positioned within the vessel at a position proximal of a stenosis of the vessel; receiving, at the processing unit, distal pressure measurements for the at least one cardiac cycle of the patient while the at least one pressure-sensing instrument is positioned within the vessel at a position distal of the stenosis of the vessel; selecting, using the processing unit, a diagnostic window within a cardiac cycle of the patient by identifying a change in sign of a slope associated with at least one of the proximal pressure measurements or the distal pressure measurements, wherein the diagnostic window encompasses only a portion of the cardiac cycle of the patient; calculating, using the processing unit, a pressure ratio between the distal pressure measurements obtained during the diagnostic window and the proximal pressure measurements obtained during the diagnostic window; and outputting, using the processing unit, the calculated pressure ratio to a display device in communication with the processing unit.

In some embodiments, the selecting a diagnostic window does not include using electrocardiogram (ECG) data. In some embodiments, the obtaining proximal pressure measurements and the obtaining distal pressure measurements do not include administering a hyperemic agent. In some embodiments, the method further includes calculating, using the processing circuit, the slope over multiple time periods within the cardiac cycle. In some embodiments, a single time period encompasses only a portion of the cardiac cycle. In some embodiments, time periods within the cardiac cycle have the same duration. In some embodiments, the method further includes calculating the slope over multiple time periods of a further cardiac cycle, wherein the time periods of the further cardiac cycle have a different duration than the time periods of the cardiac cycle. In some embodiments, a duration of the time periods is based on a duration of a cardiac cycle. In some embodiments, a duration of the time periods is based on a duration of time periods in one or more previous cardiac cycles. In some embodiments, consecutive time periods at least partially overlap in time. In some embodiments, a starting point of consecutive time periods are offset based on an acquisition rate of the at least one pressure-sensing instrument.

In some embodiments, the method further includes identifying, using the processing unit, a sign change of the slope based on the slope calculated over the plurality of time periods. In some embodiments, the method further includes determining, using the processing unit and based on the sign change of the slope, at least one of: a minimum pressure measurement, a peak pressure measurement, a beginning of the cardiac cycle, an ending of the cardiac cycle, a beginning of systole, an ending of diastole, a starting point of the diagnostic window, or an ending point of the diagnostic window. In some embodiments, the method further includes determining, using the processing unit, a starting point of the diagnostic window based on the sign change of the slope. In some embodiments, the starting point of the diagnostic window is offset from the sign change of the slope. In some embodiments, the method further includes determining, using the processing unit, a peak pressure measurement based on the sign change of the slope. In some embodiments, the peak pressure measurement is offset from the sign change of the slope. In some embodiments, the method further includes determining, using the processing unit, a starting point of the diagnostic window based on the peak pressure measurement. In some embodiments, the starting point of the diagnostic window is offset from the peak pressure measurement. In some embodiments, the method further includes determining, using the processing unit, a maximum negative slope occurring after the peak pressure measurement. In some embodiments, the method further includes determining, using the processing unit, a starting point of the diagnostic window based on the maximum negative slope. In some embodiments, the starting point of the diagnostic window is offset from the maximum negative slope. In some embodiments, the method further includes determining, using the processing unit, a further sign change of the slope. In some embodiments, the method further includes determining, using the processing unit, a minimum pressure measurement based on the further sign change of the slope. In some embodiments, the minimum pressure measurement is offset from the further sign change of the slope. In some embodiments, the method further includes determining, using the processing unit, an ending point of the diagnostic window based on the minimum pressure measurement. In some embodiments, the ending point of the diagnostic window is offset from the minimum pressure measurement.

In some embodiments, the method further includes introducing a first pressure-sensing instrument into the vessel of the patient proximal of the stenosis of the vessel; and introducing a second pressure-sensing instrument into the vessel of the patient distal of the stenosis of the vessel. In some embodiments, the receiving proximal pressure measurements includes receiving proximal pressure measurements while the first pressure-sensing instrument is positioned within the vessel at a position proximal of the stenosis of the vessel; and the receiving distal pressure measurements includes receiving distal pressure measurements while the second pressure-sensing instrument is positioned within the vessel at a position distal of the stenosis of the vessel. In some embodiments, the method further includes identifying a treatment option based on the calculated pressure ratio; and performing the identified treatment option.

Additional aspects, features, and advantages of the present disclosure will become apparent from the following detailed description.

Illustrative embodiments of the present disclosure will be described with reference to the accompanying drawings, of which:

DETAILED DESCRIPTION

Figure 1:
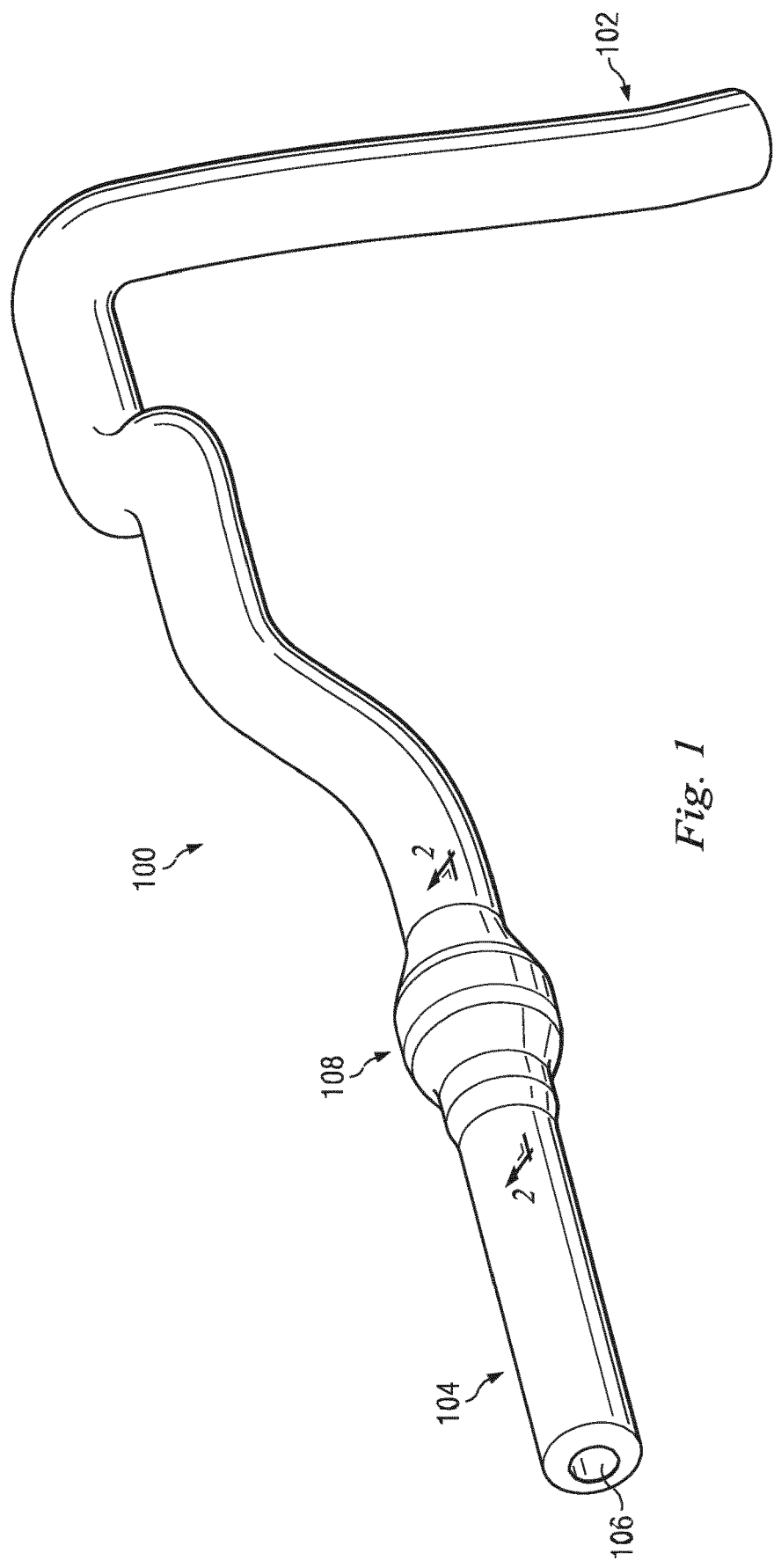
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
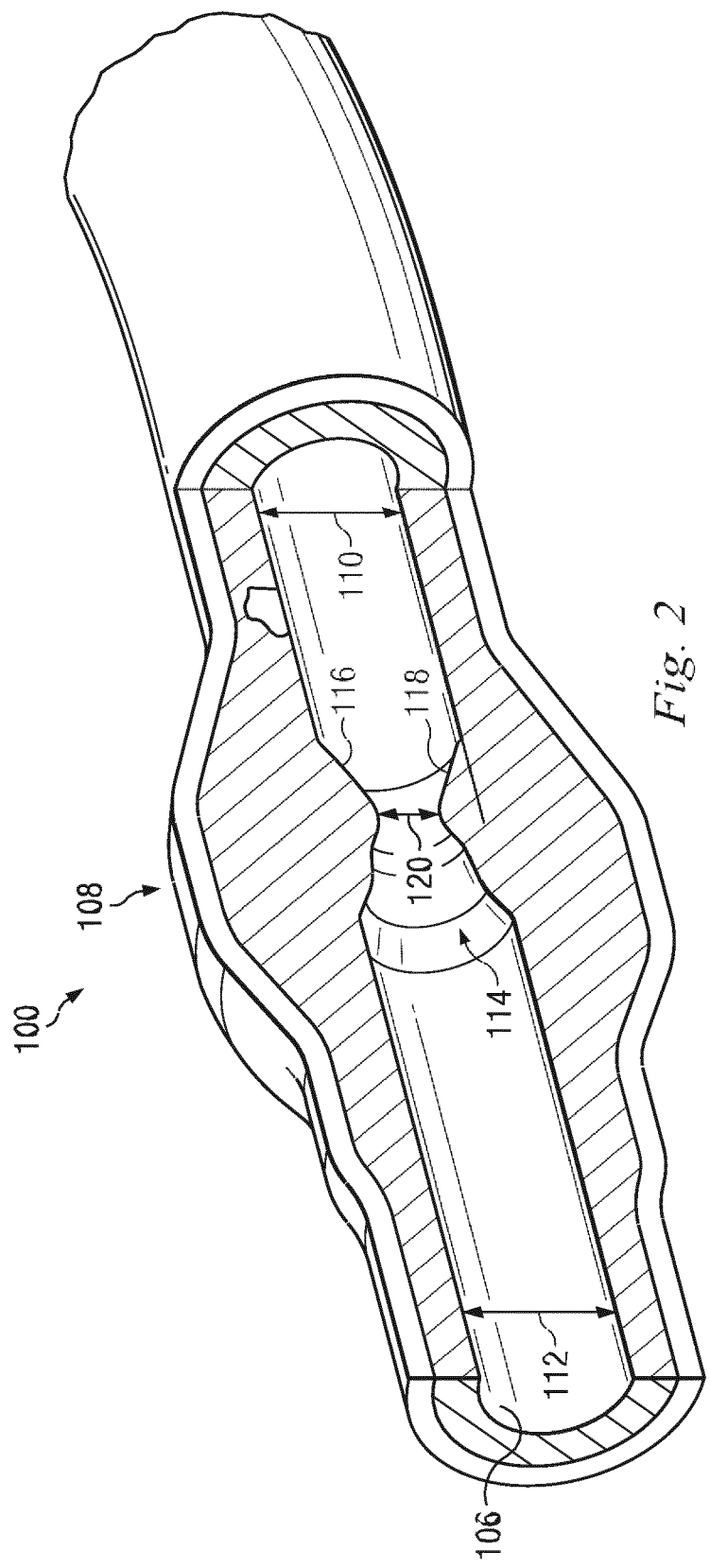
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a systemic blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
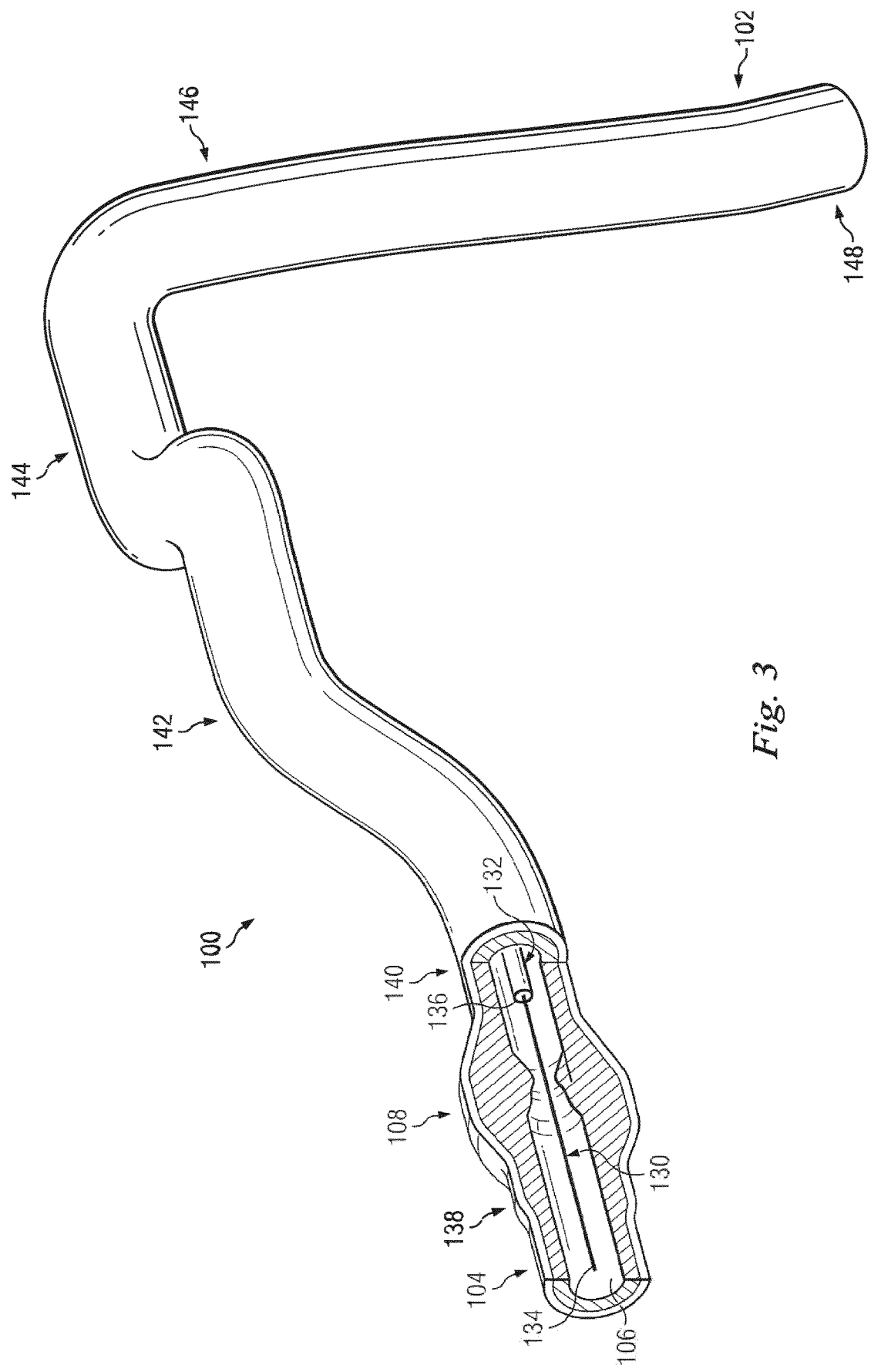
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Millar catheters are utilized in some embodiments. Currently available catheter products suitable for use with one or more of Philips's Xper Flex Cardio Physiomonitoring System, GE's Mac-Lab XT and XTi hemodynamic recording systems, Siemens's AXIOM Sensis XP VCII, McKesson's Horizon Cardiology Hemo, and Mennen's Horizon XVu Hemodynamic Monitoring System and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

Figure 4:
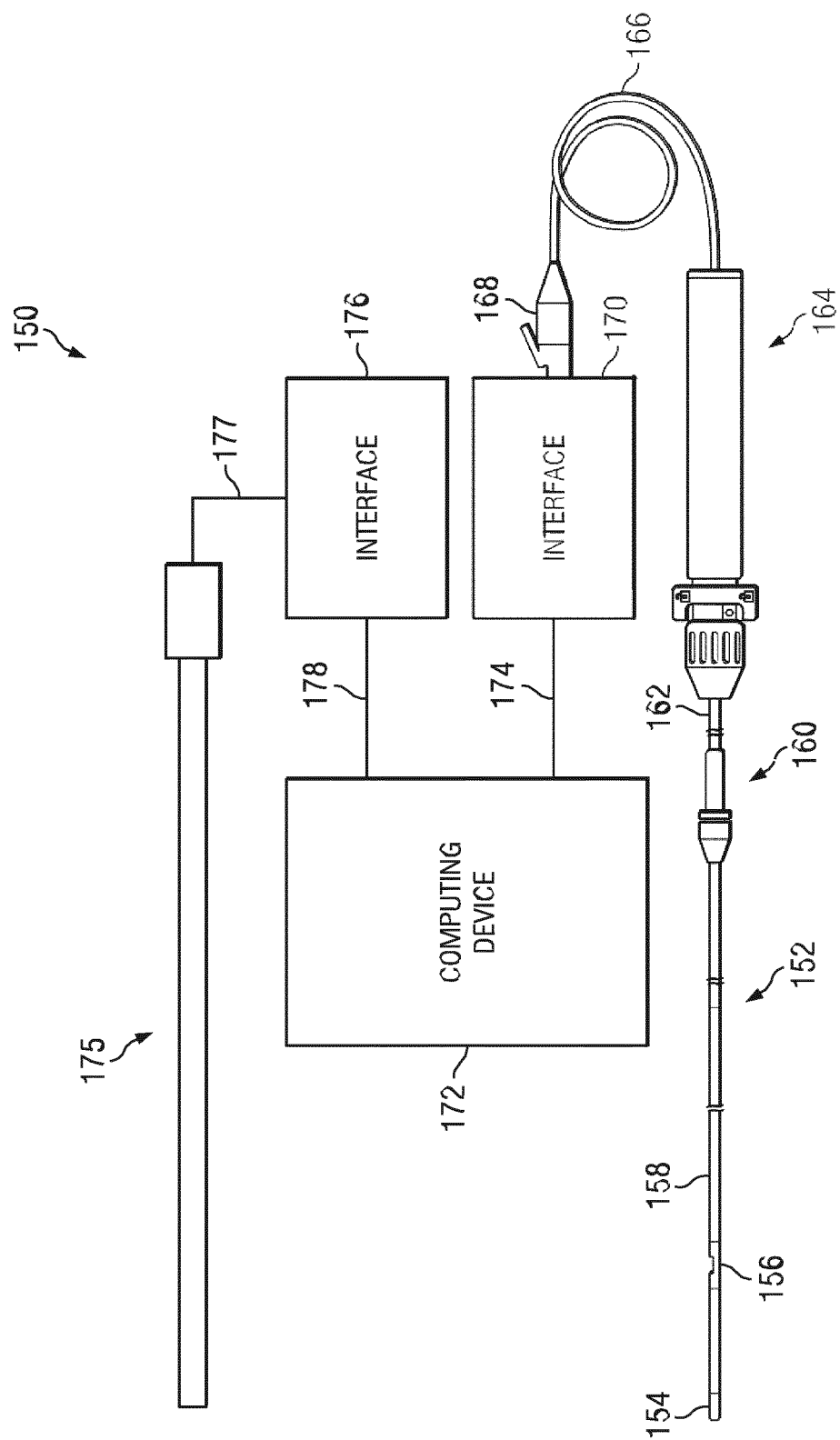
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
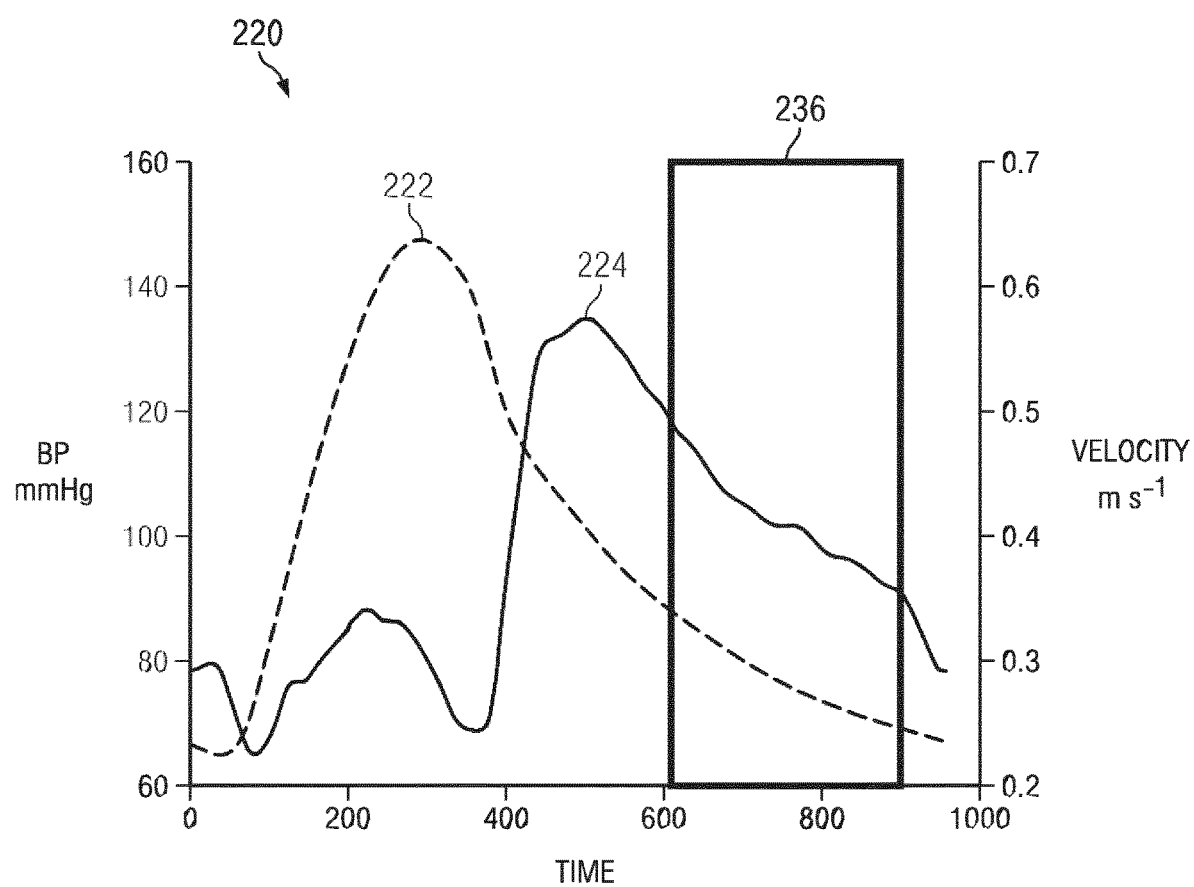
FIG. 5 is a graphical representation of measured pressure and velocity within a vessel, annotated to identify a diagnostic window, according to an embodiment of the present disclosure.

In some embodiments of the present disclose, a ratio of intravascular pressure measurements obtained during a portion of the heartbeat cycle or diagnostic window is calculated. For example, FIG. 5 includes graphical representation 220 having a plot 222 representative of pressure (measured in mmHg) within a vessel over the time period of one cardiac cycle and a plot 224 representative of velocity (measured in mls) of a fluid within the vessel over the same cardiac cycle. FIG. 5 is annotated to identify a diagnostic window 236. The diagnostic window identifies a portion of the heartbeat cycle of the patient where the resistance (e.g., pressure divided by velocity) within vasculature is reduced without the use of a hyperemic agent or other stressing technique. That is, the diagnostic window 236 corresponds to a portion of the heartbeat cycle of a resting patient that has a naturally reduced and relatively constant resistance.

The portion of the heartbeat cycle coinciding with the diagnostic window 236 can be utilized to evaluate a stenosis of the vessel of a patient without the use of a hyperemic agent or other stressing of the patient's heart. In particular, the pressure ratio (e.g., distal pressure divided by proximal pressure) across the stenosis is calculated for the time period corresponding to the diagnostic window 236 for one or more heartbeats. The calculated pressure ratio is an average over the diagnostic window in some instances. By comparing the calculated pressure ratio to a threshold or predetermined value, a physician or other treating medical personnel can determine what, if any, treatment should be administered. In that regard, in some instances, a calculated pressure ratio above a threshold value (e.g., 0.80 on a scale of 0.00 to 1.00) is indicative of a first treatment mode (e.g., no treatment, drug therapy, etc.), while a calculated pressure ratio below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters. Various aspects of the diagnostic window, including identification of the diagnostic window, features of the diagnostic window, etc., are described in U.S. application Ser. No. 13/460,296, titled "Devices, Systems, and Methods for Assessing a Vessel," and filed Apr. 30, 2012, the entirety of which is incorporated by reference herein.

Figure 6:
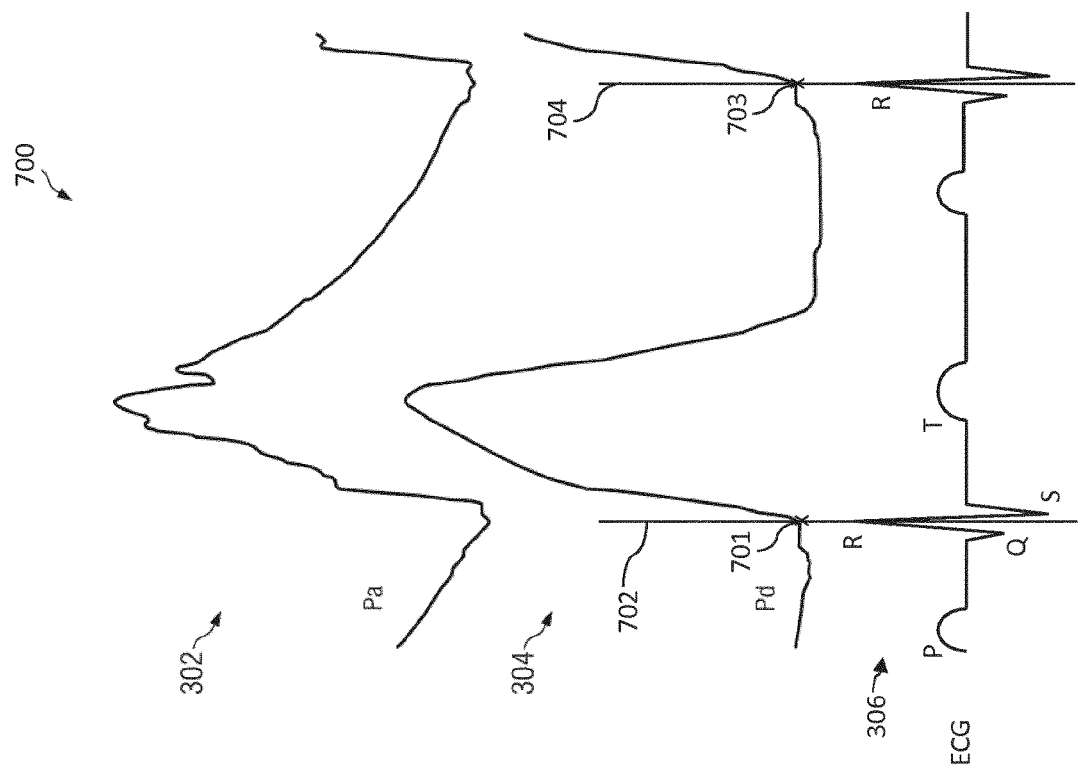
FIG. 6 is a graphical representation of identifying a feature of a pressure waveform, cardiac cycle, and/or a diagnostic window using an ECG signal.
Figure 7:
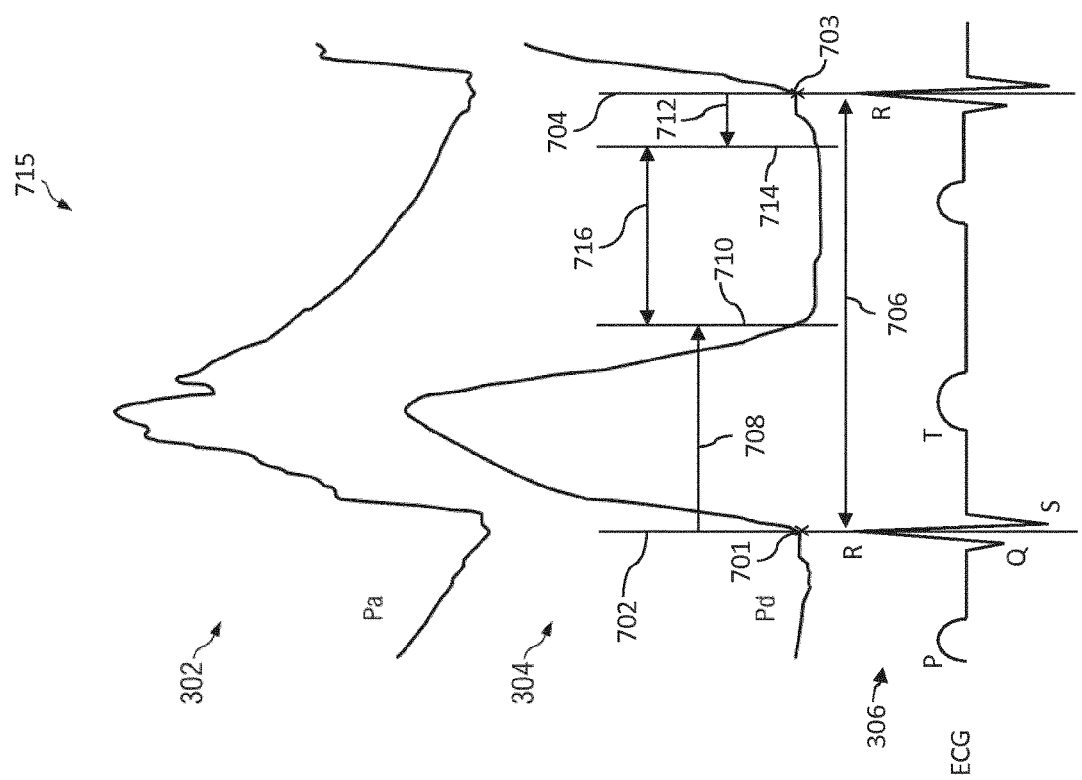
FIG. 7 is a graphical representation of a diagnostic window identified based on the feature of FIG. 6.
Figure 8:
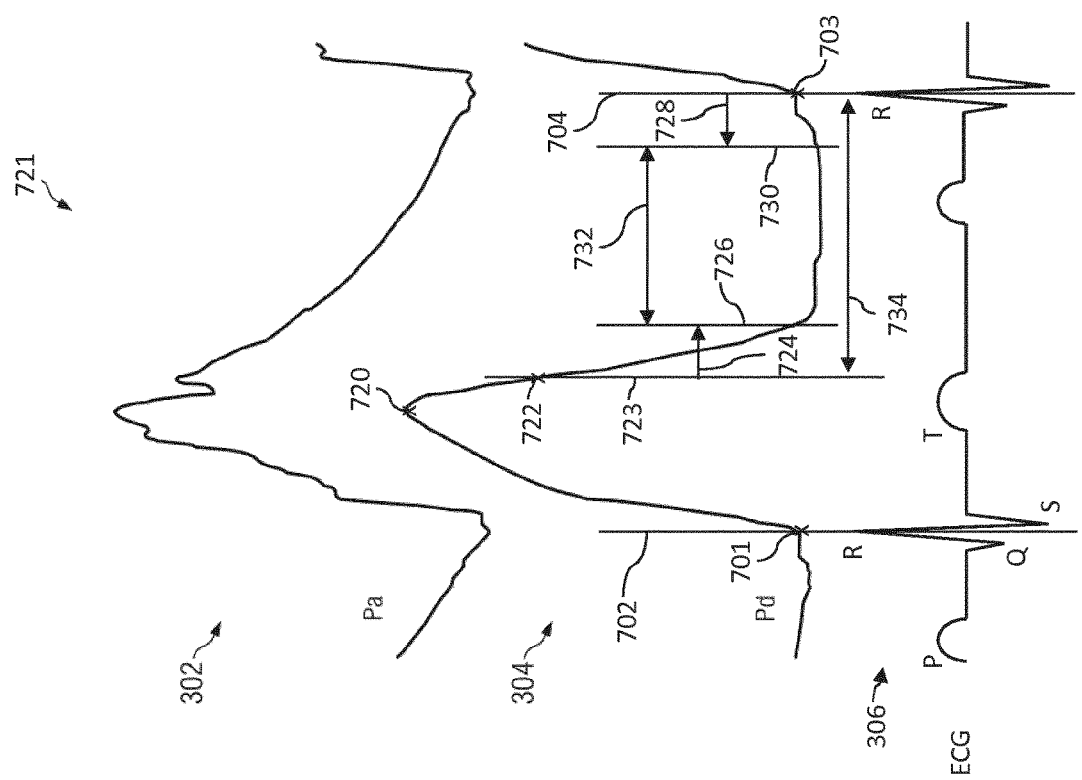
FIG. 8 is a graphical representation of a diagnostic window identified based on the feature of FIG. 6 according to another embodiment of the present disclosure

Referring now to FIGS. 6-8, shown therein are various graphical representations of techniques for determining start and/or end points for a diagnostic window in conjunction with an ECG signal in accordance with the present disclosure. The graphical representation 700 of FIG. 6 illustrates a proximal pressure waveform 302, a distal pressure waveform 304, and an associated ECG waveform 705. The proximal pressure waveform 302 and distal pressure waveform 304 are representative of proximal and distal pressure measurements obtained within the vasculature. The ECG waveform 705 is representative of an ECG signal of the patient obtained at the same time as the proximal and distal pressure measurements are obtained. In that regard, the waveforms 302, 304, 705 in FIGS. 6-8 are arranged to show how the illustrated physiological attributes are generally aligned in time.

Referring again to FIG. 6, a computing device can identify feature(s) of a diagnostic window, pressure waveform(s) 302, 304, and/or the patient's cardiac cycle based on the ECG waveform 705. For example, using the peak of the R-wave in the ECG waveform 705, the computing device can identify a minimum pressure value or valley 701, 703 for each cardiac cycle. In particular, the peak of the R-wave in the ECG waveform 705 occurs at a time 702 that corresponds to the minimum pressure value 701 in the distal pressure waveform 304. The next peak of the R-wave in the ECG waveform 705 (for the next cardiac cycle) occurs at a time 704 that corresponds to the minimum pressure value 703 in the distal pressure waveform 304. In that regard, the minimum pressure value 701 corresponds to a cardiac cycle (n), and the minimum pressure value 703 corresponds to a next cardiac cycle (n+1). The time 702 corresponds to the beginning of the cardiac cycle (n) and/or the beginning of systole (n). The time 704 corresponds to the end of the cardiac cycle (n), beginning of the next cardiac cycle (n+1), the end of diastole (n), and/or the beginning of systole (n+1). While the distal pressure waveform 304 is specifically mentioned in this discussion, it is understood that the proximal pressure waveform 302 can be similarly utilized. Generally, at least one identifiable feature of the ECG signal (including without limitation, the start of a P-wave, the peak of a P-wave, the end of a P-wave, a PR interval, a PR segment, the beginning of a QRS complex, the start of an R-wave, the peak of an R-wave, the end of an R-wave, the end of a QRS complex (J-point), an ST segment, the start of a T-wave, the peak of a T-wave, and the end of a T-wave) can utilized to select that starting point and/or ending point of the diagnostic window, identify features of the proximal or distal pressure waveforms 302, 304, etc., as described for example, in U.S. application Ser. No. 13/460,296, titled "Devices, Systems, and Methods for Assessing a Vessel," and filed Apr. 30, 2012, the entirety of which is incorporated by reference herein.

Referring now to FIG. 7, shown therein is a graphical representation 711 of selecting a diagnostic window based on the feature(s) of the pressure waveform(s) identified using the ECG signal. In some instances, the starting point 710 and/or ending point 714 of the diagnostic window 716 is determined by adding or subtracting a fixed amount of time 708, 712 to an identifiable feature of the ECG signal. In that regard, the fixed amount time 708, 712 can be a percentage of the cardiac cycle 706 in some instances. In that regard, the diagnostic window or wave-free period 716 can be identified based on the minimum pressure values 701, 703. For example, the time period 706 between the minimum pressure values 701, 703 corresponds to the duration of a cardiac cycle. A computing device can select a beginning point 710 of the diagnostic window 716 to be positioned a fixed percentage of the total cardiac cycle time 706 from the time 702. That is, the beginning point 710 of the diagnostic window can be offset by a period 708 from the time 702 of the minimum pressure value 701. A computing device can select an ending point 714 of the diagnostic window 716 to be positioned a fixed percentage of the total cardiac cycle time 706 from the time 704. That is, the ending point 714 of the diagnostic window can be offset by a period 712 from the time 704 of the next minimum pressure value 703. One, the other, or both of the periods 708, 712 can be described as a percentage of the total cardiac cycle time 706, including values between about 5% and about 95%, between about 10% and about 50%, between about 20% and 40%, such as 15%, 20%, 25%, 30%, 35%, 40%, and/or other suitable values both larger and smaller.

Referring now to FIG. 8, shown therein is a graphical representation 721 of selecting a diagnostic window based on the feature(s) of the pressure waveform(s) identified using the ECG signal, according to another embodiment of the present disclosure. In that regard, the diagnostic window or wave-free period 732 can be identified based on the minimum pressure values 701, 703. Starting from the minimum pressure value 701, a computing device can identify a peak pressure value 720 in the distal pressure waveform 304. The computing device can identify a maximum negative/down slope value 722 that occurs after the peak pressure value 720. The maximum negative/down slope value 722 identifies when the pressure waveform 304 decreases at the fastest rate. The diagnostic window 732 can be selected within the period 734 between the maximum down slope value 722 and the next minimum pressure value 703. In that regard, the computing device can select a beginning point 726 of the diagnostic window 732 to be positioned a fixed percentage of the period 734 from the time 723. That is, the beginning point 726 of the diagnostic window can be offset by a period 724 from the time 723 of the maximum down slope value 722. A computing device can select an ending point 730 of the diagnostic window 732 to be positioned a fixed percentage of the period 734 from the time 704.

That is, the ending point 730 of the diagnostic window can be offset by a period 728 from the time 704 of the next minimum pressure value 703. One, the other, or both of the periods 724, 728 can be described as a percentage of the period 734, including values between about 10% and about 90%, between about 12% and about 40%, between about 15% and 30%, such as 15%, 20%, 25%, and/or other suitable values both larger and smaller. For example, the period 724 can be 25% of the period 734, and the period 728 can be 15% of the period 734.

Referring now to FIGS. 9-14, shown therein are various graphical representations of techniques for determining start and/or end points for a diagnostic window. In particular, the algorithm described in the FIGS. 9-14 uses a segment-by-segment analysis of the pressure waveform(s) to identify feature(s) of the cardiac cycle (e.g., the beginning/ending of a cardiac cycle) and/or the pressure waveform(s) themselves (e.g., a minimum pressure value, a peak pressure value, etc.). The diagnostic window is then selected based on the identified feature(s). In that regard, an ECG signal is not used to identify the diagnostic window, a feature of the pressure waveform(s), and/or a feature of the cardiac cycle. Thus, any discomfort experienced by the patient associated with obtaining the ECG signal can be advantageously avoided.

Figure 9:
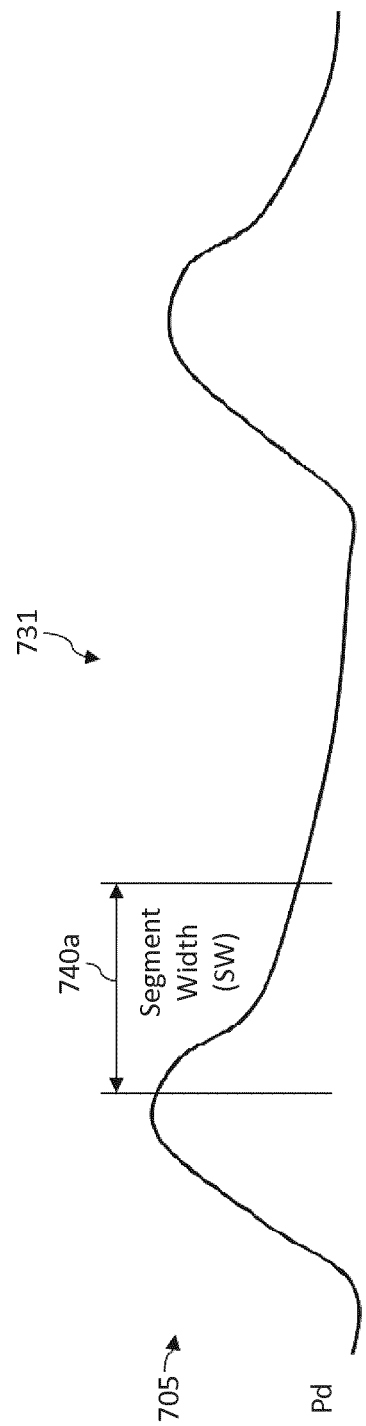
FIG. 9 is a graphical representation of a segment of a pressure waveform.

Referring now to FIG. 9, shown therein is a graphical representation 731 of a distal pressure waveform 705. As described herein, the waveform 705 is a based on distal pressure measurements obtained by an intravascular device disposed within vasculature. While a distal pressure waveform is specifically referenced in this discussion, it is understood that a proximal pressure waveform can be similarly utilized. Additionally, while the waveforms in FIG. 9 and elsewhere are shown as smooth, it is understood that the waveforms comprise discrete pressure measurement(s).

A segment 740a of the pressure waveform 705 is indicated in FIG. 9. The segment 740a identifies a portion of the pressure waveform 705, a subset of the pressure measurements associated with the pressure waveform 705, and/or a time period associated with the pressure waveform 705. As described herein, a period-by-period or segment-by-segment analysis is used to identify features of the cardiac cycle and/or the pressure waveform itself. In some instances, time period, period, and/or segment may be used interchangeably in the discussion herein. The time period or segment 740a has a segment width (SW). That is, the pressure measurements associated with the segment 740a are obtained over the given time. For example, the width or duration of the segment 740a can be less than a cardiac cycle duration, encompassing only a portion of the cardiac cycle. In various embodiments, the duration of the segment 740a compared to the cardiac cycle duration is between approximately 10% and approximately 90%, approximately 10% and approximately 50%, approximately 10% and approximately 40%, including values such as 20%, 25%, 30%, 33%, 35%, and/or other suitable values both larger and smaller. In some instances, a cardiac cycle duration can be approximately 1 second. For example, the duration of the segment 740a can be between approximately 0.1 seconds and approximately 0.9 seconds, approximately 0.1 seconds and approximately 0.5 seconds, approximately 0.1 seconds and approximately 0.4 seconds, including values such as 0.2 seconds, 0.25 seconds, 0.3 seconds, 0.33 seconds, 0.35 seconds, and/or other suitable values both larger and smaller. In some embodiments, the width or duration of the segment 740a varies for each cardiac cycle. For example, time periods associated with different cardiac cycles have different durations. In that regard, the duration of the segment 740a can be adjusted manually by a user or automatically by a computing device. For example, the duration of the segment 740a can be based on the cardiac cycle duration of the cardiac cycle. In that regard, the cardiac cycle duration can be described as the duration between consecutive peak pressure values, consecutive minimum pressure values, etc. For example, the duration of the segment 740a of a cardiac cycle (n) can be based on the duration of one or more earlier cardiac cycles (n−1, n−2, etc.) such that the duration is adaptive to a patient's heart rhythm. In some embodiments, a duration of the time periods is based on a duration of time periods in one or more previous cardiac cycles. For example, the duration of the segment 740a can an average of earlier segment durations. That is, the duration of segment 740a can be the average of multiple, prior segment durations. The number of prior segments considered can be variable, adjustable manually by a user, and/or adjustable automatically be a computing device. In some embodiments, the width or duration of the segment 740a can be defined by a quantity of pressure measurements obtained during the segment. In some embodiments, the duration of the segment 740a is bounded by a maximum duration and a minimum duration. In some embodiments, the duration of the segment 740a (e.g., relative to a cardiac cycle) is optimized during manufacture of an intravascular system, while in other embodiments, the duration of the segment can be adjusted prior to, during, and/or after an intravascular procedure.

Figure 10:
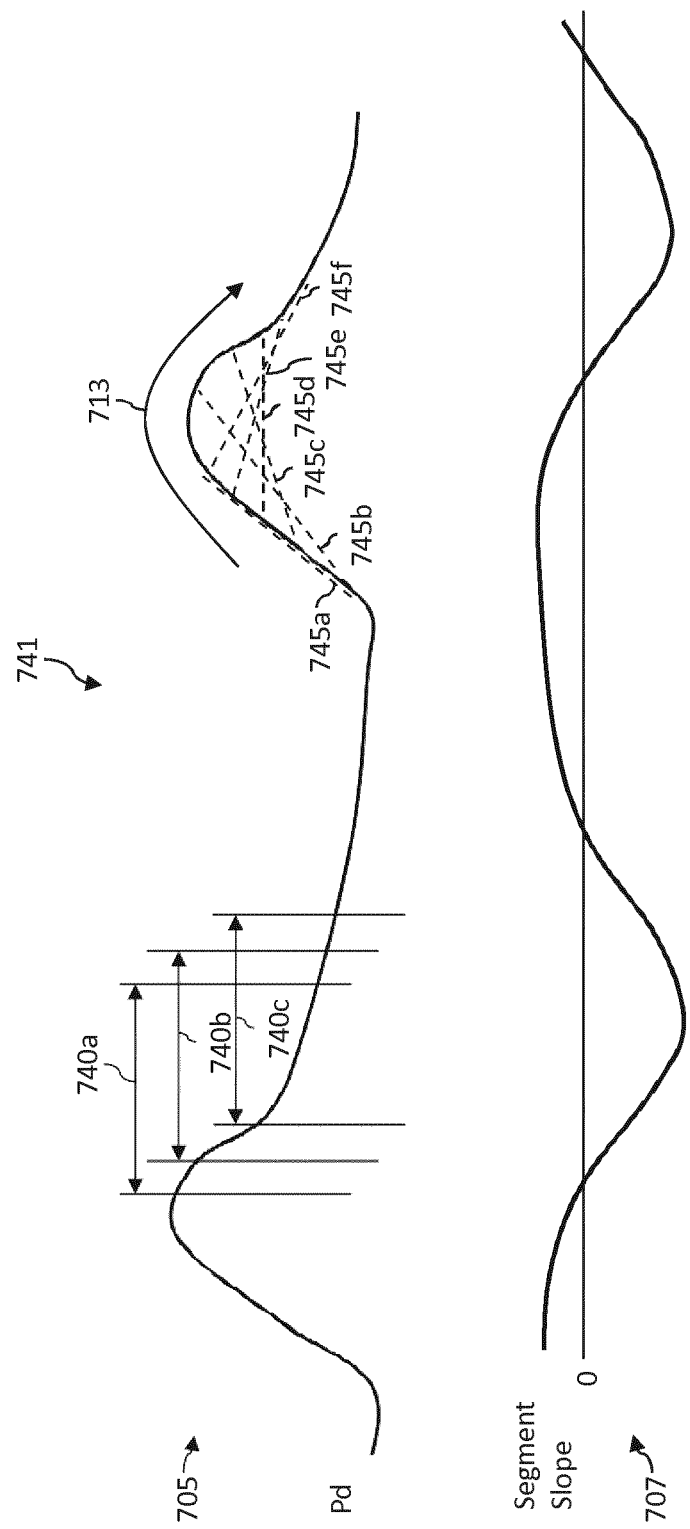
FIG. 10 is a pair of graphical representations, where the top graphical representation illustrates a segment-by-segment analysis of the pressure waveform and the bottom graphical representation illustrates a slope of the pressure waveform associated with each segment.

Referring now to FIG. 10, shown therein is a graphical representation 751 illustrating a period-by-period analysis of the pressure waveform 705. Also shown is a segment slope waveform 707 illustrating a slope of the pressure waveform 705 associated with each segment. According to an aspect of the present disclosure, a period-by-period analysis of the slope of the pressure waveform 705 is used to identify feature(s) of the cardiac cycle (e.g., the beginning/ending of a cardiac cycle) and/or the pressure waveform(s) itself (e.g., a minimum pressure value, a peak pressure value, etc.). Generally, specific patterns exist within arterial blood pressure waveforms. The patterns, such as maxima (peaks) and minima (valleys) of the pressure waveforms, can be used to identify the cardiac cycle and the wave-free diagnostic period within the cardiac cycle. In the case of healthy vasculature with a regular cardiac cycle, there are minimal artifacts in the pressure signals. Thus, the peaks and valleys of the pressure waveforms can be detected by simply finding the minimum and the maximum values, without the aid of massive filtering processes. However, the pressure signals from diseased hearts are typically distorted by abnormal heart operations (e.g., arrhythmia, premature ventricular contraction, etc.) and/or motion artifacts resulting from pressure measurement (e.g., pullback of the pressure-sensing intravascular device). Therefore, complicated filtering procedures are typically needed to remove those corruptions and to have clean pressure signals from which to visualize peaks and valleys clearly. In that regard, the algorithm described herein advantageously provides for robust identification of features of the cardiac cycle and/or pressure waveform, even in diseased vasculature and without the need for extensive signal filtering hardware or software.

FIG. 10 illustrates a plurality of period segments 740a, 740b, 740c. It is understood the segments 740a-740c are only a portion of the total number of segments used to analyze pressure waveform 705. In some embodiments, the width or duration of each segment 740a-740c is the same for a given cardiac cycle. For example, time periods associated with a single cardiac cycle have the same duration. In some embodiments, the each of the segments 740a-740c are consecutive or adjacent in time. For example, a beginning point, midpoint, and/or ending point of the segments 740a, 740b, 740c can be adjacent in time. For example, every subsequent pressure sample may define the beginning of a different segment. Each of the segments 740a-740c can be defined by a starting time, ending time, and/or midpoint time. Consecutive segments can be separated by a period between about 0.001 seconds and about 0.5 seconds, about 0.001 seconds and 0.1 seconds, and/other suitable values both larger and smaller, including the time between consecutive pressure measurements. In some embodiments, a starting point of consecutive time periods or segments can be offset based on an acquisition rate of an intravascular pressure-sensing device. For example, data can be acquired from the pressure-sensing instrument for 1 ms every 5 ms and/or other suitable rates. Consecutive time periods can be offset by about 5 ms in such embodiments and/or other suitable times in different embodiments. In some embodiments, the segments 740a-740c are overlapping in time. In that regard, the segments 740a-740c can overlap by any suitable amount of time. In some embodiments, the time period associated with the overlap can be adjusted manually by a user or automatically by a computing device. In some embodiments, the overlap can be defined by a quantity of pressure measurements. It is understood that the overlap between segments 740a-740c illustrated in FIG. 10 is exemplary, and other overlap times, both larger and smaller, are contemplated.

The segment slope waveform 707 is a plot of the slope of each time period or segment (such as segments 740a-740c) of the pressure waveform 705. In some embodiments, a computing device can calculate the slope of the pressure waveform 705 calculated at each pressure sample. The slope may be an average slope of the segment, an instantaneous slope of the segment (e.g., at the beginning point, a midpoint, and/or the ending point), and/or other suitable quantity. For the example, the slope may be calculated as a change/difference in two pressure measurements divided by the change/difference in time between the two pressure measurements. In that regard, with a sufficiently wide segment width and with an average slope calculated across the entire duration of the segment, the slope is advantageously less sensitive to the distorted high and low frequency peaks resulting from abnormal vasculature conditions or motion artifacts from pressure measurements. In some embodiments, the sample location where the average slope is calculated is at or near the sample in the middle of the segment. For example, the average slope, at the midpoint of the segment, may be calculated as the change/difference in the pressure measurement between the starting point and the ending point of the segment divided by the change/difference in time between the starting and ending points. As illustrated in FIG. 10, the value of the segment slope waveform 707 changes along the pressure waveform 705 as, e.g., the average slope of each segment of the pressure waveform 705 is determined. In some instances, the sign or polarity of the segment slope waveform 707 switches between positive and negative (or vice versa).

The slope of multiple time periods or segments 745a, 745b, 745c, 745d, 745e, 745f is also illustrated in FIG. 10. In that regard, each of the segments 745a-745f is represented by a linear segment spanning its associated pressure measurements on the pressure waveform 705. That is, the length of the linear segments can correspond to the duration or width of the segments 745a-745f. As described with respect to segments 740a-740c, for a given cardiac cycle, the segments 745a-745f have equal width or span the same amount of time. The linear segments are also shown as angled to match the average slope associated with the segments 745a-745f. For example, the segment 745a spans a portion of the pressure waveform 705 having a generally positive slope. Correspondingly, the linear segment for segment 745a is shown having a generally positive slope. Segments 745b-745f variously span different portions the pressure waveform 705 that having positive slope, zero slope, and/or negative slope. As the influence of the zero slope or negative slope portions increases (towards the right of pressure waveform 705), the linear segments are illustrated as having less positive slope than segment 745a. For example, segments 745b, 745c span portions of the pressure waveform 705 having zero slope and negative slope. Thus, the linear segment associated with segments 745b, 745c have a less positive slope, compared to the linear segment associated with segment 745a, which only spans portions of the pressure waveform 705 having positive slope. Segment 745d spans portions of the pressure waveform 705 with an average slope of zero. Thus, the linear segment is illustrated as having zero slope. Segments 745e and 745f span relatively larger portions of the pressure waveform 705 with negative slope, and, thus, the corresponding linear segments have negative slopes. The corresponding slope values are plotted in the segment slope waveform 707. Generally, the slope of the segments 745a-745f changes in the direction indicated by arrow 713. The portion of the pressure waveform 705 spanned by the segments 745a-745f includes a change in slope sign. This is illustrated by the linear segments for segments 745a-745f changing slope from positive to negative. Likewise, the segment slope waveform 707 corresponding to the area of segments 745a-745f starts positive, crosses the zero line, and becomes negative.

Figure 11:
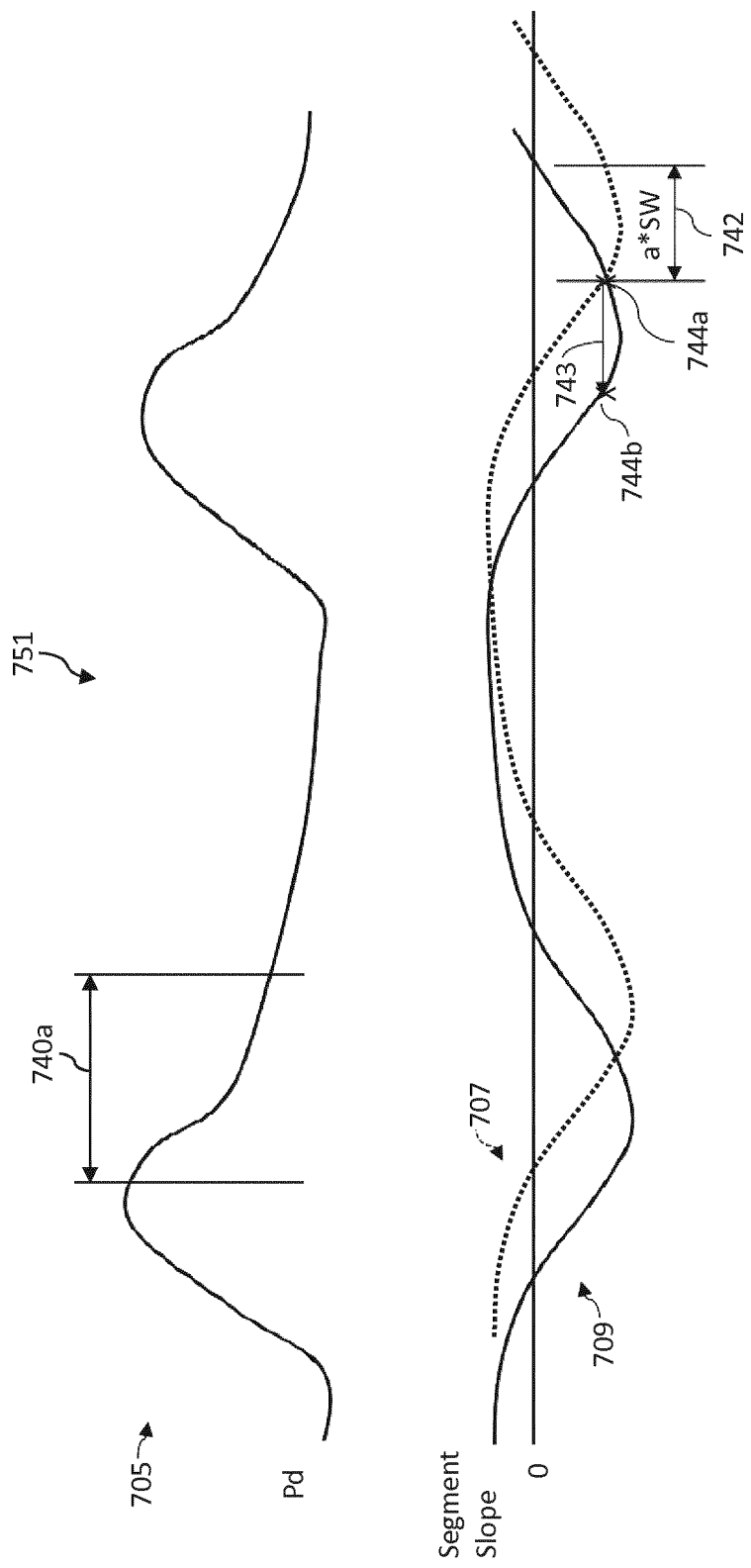
FIG. 11 is a pair of graphical representations similar to that of FIG. 10, but where the segment slope waveform of the bottom graphical representation has been shifted relative the segment slope waveform of FIG. 10.

Referring now to FIG. 11, shown therein is a graphical representation 751 including the pressure waveform 705 and segment slope waveform 707, similar to that of graphical representation 741 (FIG. 10). Graphical representation 751 also includes a segment slope waveform 709 that is offset from the segment slope waveform 707 by a period 742. In that regard, the period 742 can correspond to a calculation delay in embodiments in which the segment slope is calculated around the pressure sample at or near middle of the segment 740a. Thus, in such embodiments, the first segment slope is calculated only after approximately half of the duration of the segment 740a. In general, the period 742 can be described as a multiple of the segment width (a*SW). In that regard, the multiple can be greater than, equal to, or less than one (a>1, a=1, or a<1) in different embodiments. For example, the multiple (a) can be between about 0.01 and about 0.99, about 0.1 and about 0.9, about 0.3 and about 0.7, including values such as 0.35, 0.4, 0.45, 0.5, 0.55, 0.6, 0.65, and/or other suitable values both larger and smaller. FIG. 11 illustrates that values of the segment slope waveform 707 can be shifted to account for the calculation delay. For example, the slope 744a is shifted in the direction 743 by a time equaling the period 742, which yields the slope 744b. The shifted segment slope waveform 709 results when all values for the segment slope waveform 707 are similarly modified. In some embodiments, the algorithm described herein that identifies features of the diagnostic window, cardiac cycle, and/or the pressure waveform utilizes the shifted waveform 709.

Figure 12:
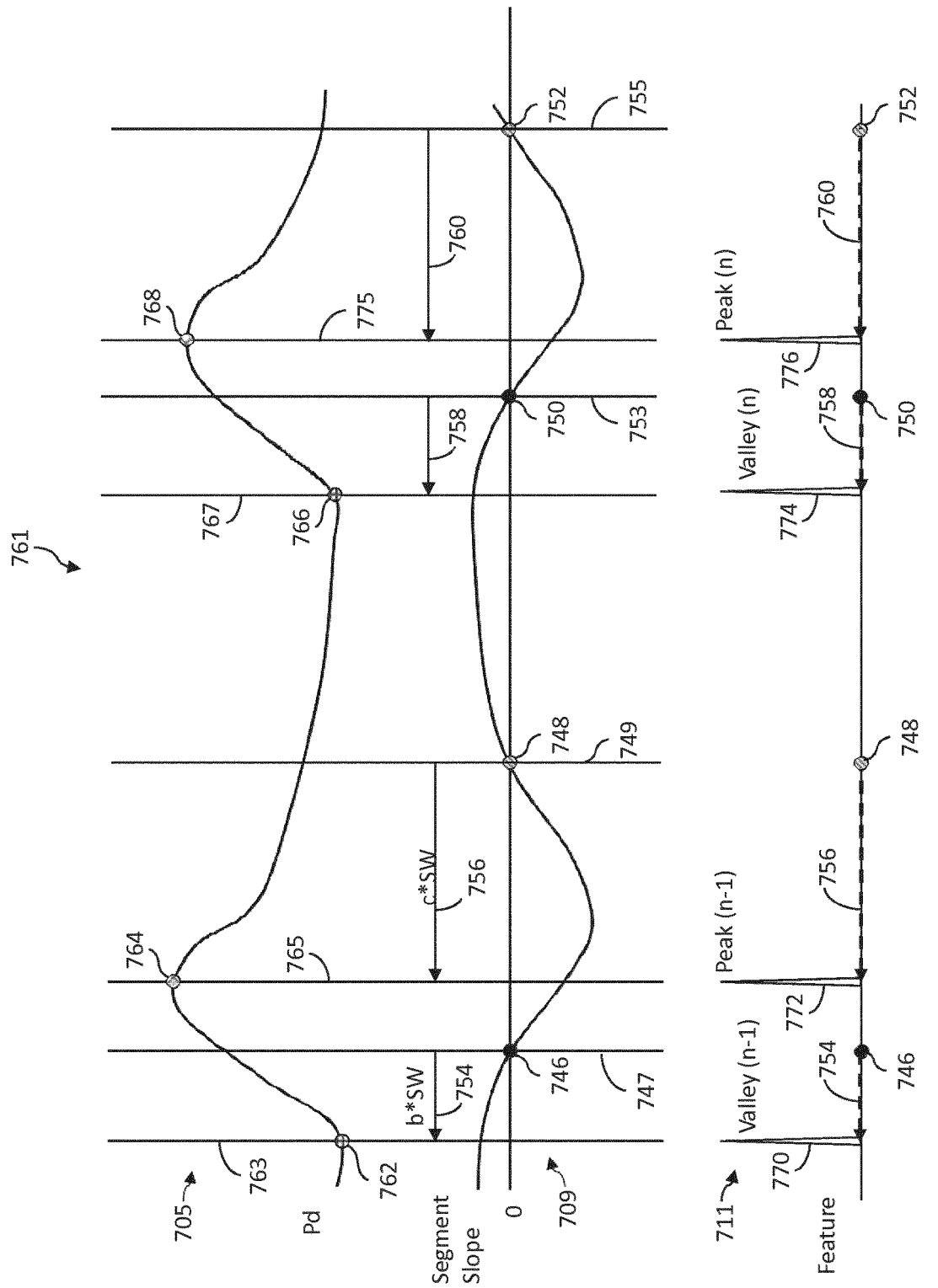
FIG. 12 is a graphical representation of identifying a feature of a pressure waveform, a cardiac cycle, and/or a diagnostic window, using the segment slope waveform.

Referring now to FIG. 12, shown therein a graphical representation 761 including the pressure waveform 705 and the segment slope waveform 709. Also illustrated is a feature plot 711, identifying when minima (valley) and maxima (peak) of the pressure waveform 705 occur. In that regard, the waveforms 705, 709, 711 in FIG. 12 and elsewhere are arranged show alignment in time or the simultaneous occurrence of one or more physiological attributes. According to aspects of the present disclosure, the minima 762, 766 and maxima 764, 768 of the pressure waveform 705 are identified based on when the sign changes in segment slope waveform 709. The minima 762 (n−1) of the pressure waveform 705 can correspond to the beginning of the cardiac cycle (n−1) and/or the beginning of systole (n−1). The next minima 766 (n) can correspond to the end of the cardiac cycle (n−1), the end of diastole (n−1), the beginning of the cardiac cycle (n), and/or the beginning of systole (n). Thus, the features of the cardiac cycle can also be identified based on when sign changes in segment slope waveform 709. Correspondingly, the diagnostic window (e.g., the beginning, the ending, etc.) can be selected based on when the sign changes in segment slope waveform 709.

The sign of the segment slope waveform 709 changes at times 747, 749, 753, 755. In particular, the sign of the segment slope waveform 709 changes from positive to negative at times 747 and 753. The locations 746, 750 in segment slope waveform 709 correspond to these positive to negative sign changes. The minima 762, 766 of the pressure waveform 705 can be identified based on the location the sign of the segment slope waveform 709 changes from positive to negative. For example, the minimum 762 can occur at a time 763, prior to the time 747 associated with the sign change 746. In an embodiment, the time 763 occurs at half of the segment width before the time 747. Thus, the minimum 762 is offset from the sign change 746. Generally, the period 754 separating the positive-to-negative sign change and the minimum pressure measurement can be a multiple of the segment width (b*SW). In that regard, the multiple can be greater than, equal to, or less than one (b>1, b=1, or b<1) in different embodiments. For example, the multiple (c) can be between about 0.01 and about 2, about 0.1 and about 0.9, about 0.3 and about 0.7, including values such as 0.35, 0.4, 0.45, 0.5, 0.55, 0.6, 0.65, and/or other suitable values both larger and smaller. Similarly, the minimum 766 can occur at a time 767, prior to the time 753 associated with the sign change 750. Thus, the minimum 766 is offset from the sign change 750. The period 758 separating the times 753, 767 can be a multiple of the segment width. In that regard, because the minima 762, 766 are associated with different heart beat cycles, the periods 754, 758 can be different in some instances.

The value of the segment slope waveform 709 changes from negative to positive at times 749 and 755. The locations 748, 752 in segment slope waveform 709 correspond to these negative-to-positive sign changes. The maxima 764, 768 of the pressure waveform 705 can be identified based on the location the sign of the segment slope waveform 709 changes from negative to positive. For example, the maximum 764 can occur at a time 765, prior to the time 749 associated with the sign change 748. In an embodiment, the time 765 occurs at 125% of the segment width before the time 749. Thus, the maximum 764 can be offset from the sign change 748. Generally, the period 756 separating the negative-to-positive sign change and the peak pressure measurement can be a multiple of the segment width (c*SW). In that regard, the multiple can be greater than, equal to, or less than one (c>1, c=1, or c<1) in different embodiments. For example, the multiple (c) can be between about 0.1 and about 2, about 1 and about 2, about 1.1 and about 1.5, including values such as 1.1, 1.2, 1.25, 1.3, 1.35, 1.4, and/or other suitable values both larger and smaller. Similarly, the maximum 768 can occur at a time 775, prior to the time 755 associated with the sign change 752. Thus, the maximum 768 can be offset from the sign change 752. The period 760 separating the times 755, 775 is a multiple of the segment width. In the regard, because the maxima 764, 768 are associated with different heart beat cycles, the periods 756, 760 can be different in some instances.

The feature plot 711 illustrates the location of the minima (valley) and maxima (peak) of the pressure waveform 705. In that regard, the valley (n−1) 770, associated with a cardiac cycle (n−1), is aligned with the time 763 that occurs a period 754 before the positive-to-negative sign change 746. The valley (n) 774, associated with the next cardiac cycle (n), is aligned with the time 767 that occurs a period 758 before the positive-to-negative sign change 750. The peak (n−1) 764, associated with a cardiac cycle (n−1), is aligned with the time 765 that occurs a period 756 before the negative-to-positive sign change 748. The peak (n) 768, associated with the next cardiac cycle (n), is aligned with the time 775 that occurs a period 760 before the negative-to-positive sign change 752.

Figure 13:
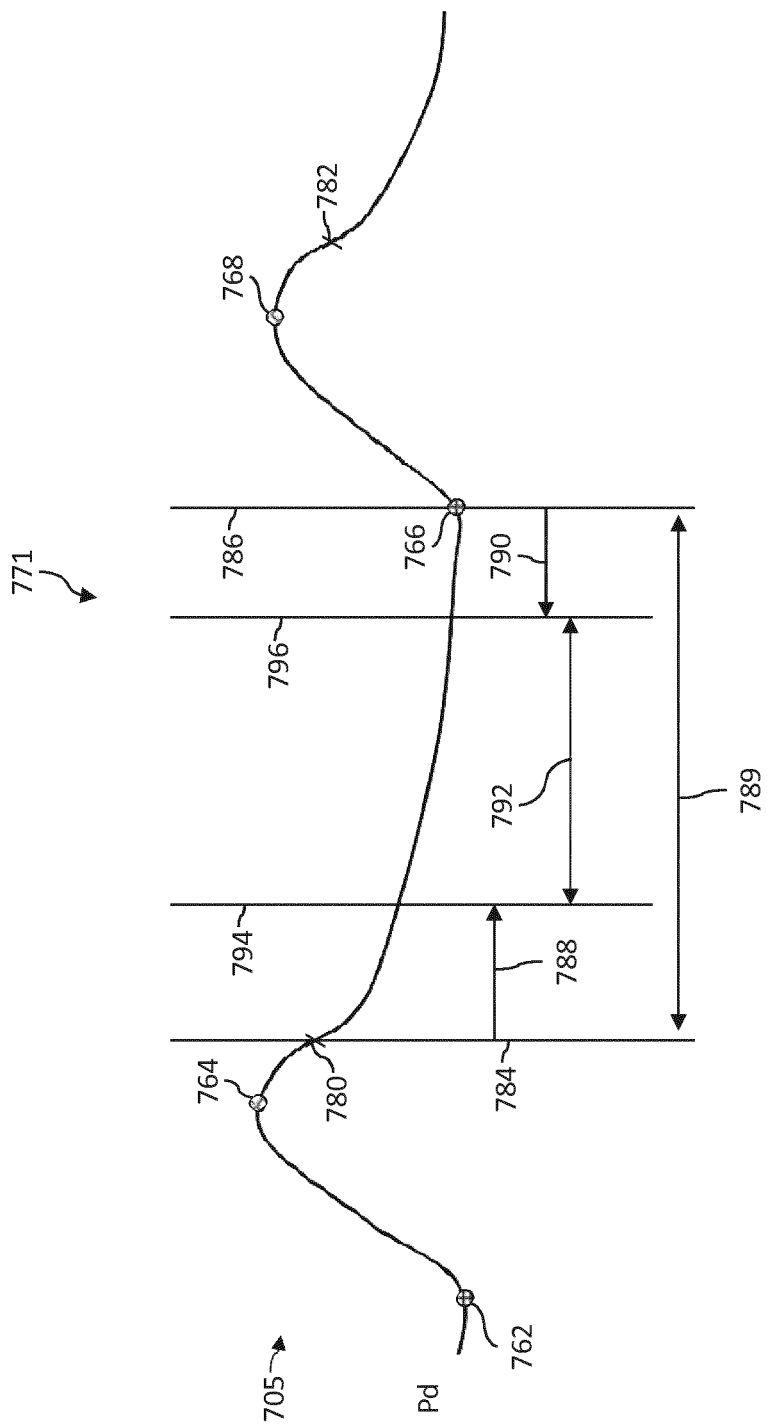
FIG. 13 is a graphical representation of identifying a diagnostic window based on the feature of FIG. 12.

Referring now to FIG. 13, shown therein is a graphical representation 771 of selecting the diagnostic window 792. The starting point 794 and/or the ending point 796 of the diagnostic window 792 can be selected based on the sign change(s) of the slope. For example, the diagnostic window can be selected using the identified minima 762, 766 and maxima 764, 768 based on the sign change(s) in the slope of the pressure waveform. In some embodiments, the starting point 794 of the diagnostic window 792 can be offset from the peak pressure measurement, and the ending point 796 can be offset from the minimum pressure measurements. In some embodiments, the starting point 794 and/or the ending point 796 can selected based on different slope sign changes. For example, the starting point 794 can be selected based on a negative-to-positive slope sign change, and the ending point 796 can be selected based on a positive-to-negative slope sign change. In some embodiments, the starting point 794 can be offset from the negative-to-positive sign change, and the ending point 796 can be offset from the positive-to-negative sign change.

In some embodiments, a computing device can identify the maximum negative/down slope 780 that occurs after the maximum or peak pressure value 764. The diagnostic window 792 can be selected within the period 789 between the maximum negative/down slope value 780 and the next minimum pressure value 766. In that regard, the computing device can select a beginning point 794 of the diagnostic window 792 to be positioned a fixed percentage of the period 789 from the time 784. That is, the beginning point 794 of the diagnostic window can be offset by a period 788 from the time 784 of the maximum negative/down slope value 780. A computing device can select an ending point 796 of the diagnostic window 792 to be positioned a fixed percentage of the period 789 from the time 786. That is, the ending point 796 of the diagnostic window can be offset by a period 790 from the time 786 of the next minimum pressure value 766. One, the other, or both of the periods 788, 790 can be described as a percentage of the period 789, including values between about 10% and about 90%, between about 12% and about 40%, between about 15% and 30%, as 15%, 20%, 25%, and/or other suitable values both larger and smaller. For example, the period 788 can be 25% of the period 789, and the period 790 can be 15% of the period 789.

Figure 14:
FIG. 14 is a flow diagram of a method of evaluating a vessel of a patient.

Referring now to FIG. 14, shown therein is flow diagram of a method 800 of evaluating a vessel of a patient. As illustrated, the method 800 includes a number of enumerated steps, but implementations of the method 800 may include additional steps before, after, and in between the enumerated steps. In some implementations, one or more of the enumerated steps may be omitted or performed in a different order. One or more of the steps of the method 800 may be performed by processing unit or processor, such as the computing device 172 (FIG. 4). One or more of the steps of the method 800 can be carried out by a user, such as a cardiologist or other medical professional.

At step 805, the method 800 includes introducing a first intravascular pressure-sensing instrument into a vessel of a patient proximal of a stenosis of vessel. In some embodiments, a catheter, guide wire, or a guide catheter with a pressure sensor can be inserted into, e.g., a coronary artery such that at least a portion of the instrument (e.g., the portion including the pressure sensor) is positioned proximal of a stenosis of the vessel. At step 810, the method 800 includes introducing a second intravascular pressure-sensing instrument into the vessel distal of the stenosis of the vessel. In some embodiments, a catheter, guide wire, or a guide catheter with a pressure sensor can be inserted into, e.g., a coronary artery such that at least a portion of the instrument (e.g., the portion including the pressure sensor) is positioned distal of the stenosis of the vessel. In some embodiments, the intravascular pressure-sensing instrument positioned proximally of the stenosis is a catheter or guide catheter, and the intravascular pressure-sensing instrument positioned distally of the stenosis is a guide wire.

At step 815, the method 800 includes receiving, at a computing device of an intravascular processing system, proximal and distal pressure measurements respectively obtained by first and second intravascular pressure-sensing instruments. The computing device is in communication with first and second intravascular pressure-sensing instruments. The proximal and distal pressure measurements can be obtained during one or more cardiac cycles of the patient. The proximal and distal pressure measurements can be obtained without administration of a hyperemic agent to the patient.

At step 820, the method 800 includes selecting, by the computing device of the intravascular processing system, a diagnostic window within the cardiac cycle of the patient. The diagnostic window encompasses only a portion of the cardiac cycle of the patient. In some embodiments, the selecting a diagnostic window does not include using electrocardiogram (ECG) data to, e.g., identify a beginning of a cardiac cycle. The diagnostic window can be selected by identifying a change in sign of a slope associated with at least one of the proximal pressure measurements or the distal pressure measurements. In that regard, the method 800 can include calculating the slope over multiple time periods. In some embodiments, a single time period encompasses only a portion of the cardiac cycle. In some embodiments, time periods associated with a single cardiac cycle have the same duration. In some embodiments, a computing device or processing unit calculates the slope over time periods of multiple cardiac cycles. The time periods associated with a first cardiac cycles can have different duration than the time periods associated with the second cardiac cycle. In some embodiments, a duration of the time periods is based on a duration of time periods in one or more previous cardiac cycles. In some embodiments, a duration of a time period is based on an average of earlier time period durations. In some embodiments, consecutive time periods at least partially overlap in time. In some embodiments, a starting point of consecutive time periods are offset based on an acquisition rate of the at least one pressure-sensing instrument.

The method 800 can include identifying a sign change of the slope based on the slope calculated over the plurality of time periods. That is, slopes respectively associated with the plurality of segments can change polarity or sign from positive to negative or from negative to positive. The method 800 can include determining, based on the sign change of the slope, a minimum pressure measurement, a peak pressure measurement, a beginning of the cardiac cycle, an ending of the cardiac cycle, a beginning of systole, an ending of diastole, a starting point of the diagnostic window, and/or an ending point of the diagnostic window.

In some embodiments, the diagnostic window can be selected based on the time during the cardiac cycle at which the sign of the slopes changes. A computing device or processing unit can determine a starting point of the diagnostic window based on the sign change of the slope. The starting point of the diagnostic window can be offset from the sign change of the slope. In some embodiments, a peak pressure measurement can be determined based on the sign change of the slope. The peak pressure measurement can be offset from the sign change of the slope. A computing device or processing unit can determine a starting point of the diagnostic window based on the peak pressure measurement. The starting point of the diagnostic window can be offset from the peak pressure measurement. In some embodiments, the method 800 further determining a maximum negative slope occurring after the peak pressure measurement. For example, the maximum negative slope point can occur between an identified peak pressure measurement (cardiac cycle n−1) and a next identified minimum pressure measurement (cardiac cycle n). A computing device or processing unit can determine a starting point of the diagnostic window based on the maximum negative slope. The starting point of the diagnostic window can be offset from the maximum negative slope.

In some embodiments, the method 800 further includes determining a second or further sign change of the slope. A computing device or processing unit can determine a minimum pressure measurement based on the further sign change of the slope. The minimum pressure measurement can be offset from the further sign change of the slope. A computing device or processing unit can determine an ending point of the diagnostic window based on the minimum pressure measurement. The ending point of the diagnostic window can be offset from the minimum pressure measurement.

At step 825, the method 800 includes identifying, by the computing device of the intravascular processing system, a plurality of the distal pressure measurements obtained during the diagnostic window from the received distal pressure measurements. The plurality of distal pressure measurements are selected based on the selected diagnostic window and are a subset of the received distal pressure measurements. Step 825 similarly includes identifying, by the computing device of the intravascular processing system, a plurality of the proximal pressure measurements obtained during the diagnostic window from the received proximal pressure measurements. The plurality of proximal pressure measurements are selected based on the selected diagnostic window and are a subset of the received proximal pressure measurements. An example of identifying a plurality of the pressure measurements obtained during the diagnostic window is described in U.S. application Ser. No. 13/460,296, titled "Devices, Systems, and Methods for Assessing a Vessel," and filed Apr. 30, 2012, the entirety of which is incorporated by reference herein.

At step 830, the method 800 includes calculating, by computing device, a pressure ratio between an average of the plurality of distal pressure measurements obtained during the diagnostic window and an average of the plurality of proximal pressure measurements obtained during the diagnostic window. An example of calculating the pressure ratio is described in U.S. application Ser. No. 13/460,296, titled "Devices, Systems, and Methods for Assessing a Vessel," and filed Apr. 30, 2012, the entirety of which is incorporated by reference herein.

At step 835, the method 800 includes outputting the calculated pressure ratio to display device in communication with computing device. In some embodiments, the proximal and distal pressure measurements are aligned (with respect to time) before the pressure ratio is calculated, as described, for example, in U.S. application Ser. No. 14/157,404, titled "Devices, Systems, and Methods for Assessing a Vessel," and filed Jan. 16, 2014; and/or U.S. application Ser. No. 13/460,296, titled "Devices, Systems, and Methods for Assessing a Vessel," and filed Apr. 30, 2012, the entireties of which is incorporated by reference herein. For example, alignment can be performed when the user selects a normalization option provided by the intravascular system. Once the normalization is ordered, the amount of misalignment is calculated by cross-correlating the proximal and distal pressure measurements pressure for every heart cycle until the fifth cycle. To complete the normalization, the pressure measurements, for each heart cycle, can be shifted by an average of the five cycles.

At step 840, the method 800 includes identifying a treatment option based on the calculated pressure ratio. For example, the treatment option can be no treatment, drug therapy, a percutaneous coronary intervention (PCI), such as angioplasty and/or stenting, a coronary artery bypass grafting (CABG) procedure, and/or other suitable clinical interventions including combinations of the foregoing options. At step 845, the method 800 includes performing the identified treatment option.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular system comprising:
at least one pressure-sensing instrument sized and shaped for introduction into a vessel of a patient;
a processor in communication with the at least one pressure-sensing instrument, the processor configured to:
obtain proximal pressure measurements for a cardiac cycle of the patient from the at least one pressure-sensing instrument while the at least one pressure-sensing instrument is positioned within the vessel at a position proximal of a stenosis of the vessel;
obtain distal pressure measurements for the cardiac cycle of the patient from the at least one pressure-sensing instrument while the at least one pressure-sensing instrument is positioned within the vessel at a position distal of the stenosis of the vessel;
calculate, for the cardiac cycle, a plurality of slopes of at least one of the proximal pressure measurements or the distal pressure measurements for a plurality of time periods within the cardiac cycle, each slope of the plurality of slopes corresponding to a time period of the plurality of time periods, wherein consecutive time periods of the plurality of time periods partially overlap within the cardiac cycle;
select a diagnostic window within the cardiac cycle of the least one cardiac cycle by identifying a change in sign of the plurality of slopes, wherein the diagnostic window encompasses only a portion of the cardiac cycle of the patient;
calculate a pressure ratio between the distal pressure measurements obtained during the diagnostic window and the proximal pressure measurements obtained during the diagnostic window; and
output the calculated pressure ratio to a display device in communication with the processor.

2. The system of claim 1, wherein a duration of the time periods is based on a duration of time periods in one or more previous cardiac cycles.

3. The system of claim 1, wherein a starting point of consecutive time periods are offset based on an acquisition rate of the at least one pressure-sensing instrument.

4. The system of claim 1, wherein the processor is further configured to determine, based on the sign change of the slope, at least one of:
a minimum pressure measurement, a peak pressure measurement, a beginning of the cardiac cycle, an ending of the cardiac cycle, a beginning of systole, an ending of diastole, a starting point of the diagnostic window, or an ending point of the diagnostic window.

5. The system of claim 1, wherein the processor is configured to determine a starting point of the diagnostic window based on the sign change of the slope, wherein the starting point of the diagnostic window is offset form the sign change of the slope.

6. The system of claim 5, wherein the processor is configured to determine a peak pressure measurement based on the sign change of the slope, wherein the peak pressure measurement is offset from the values of the slope waveform providing the sign change of the slope.

7. The system of claim 5, wherein the processor is configured to determine a peak pressure measurement based on the sign change of the slope and a starting point of the diagnostic window based on the peak pressure measurement, wherein the starting point of the diagnostic window is offset from the peak pressure measurement.

8. The system of claim 7, wherein the processor is configured to determine a peak pressure measurement based on the sign change of the slope and is further configured to determine a maximum negative slope occurring after the peak pressure measurement.

9. The system of claim 8, wherein the processor is further configured to determine a starting point of the diagnostic window based on the maximum negative slope.

10. The system of claim 9, wherein the starting point of the diagnostic window is offset from the maximum negative slope.

11. The system of claim 1, wherein a duration of each time period of the plurality of time periods is only a portion of a duration of the cardiac cycle.

12. The system of claim 1, wherein each slope of the plurality of slopes is representative of a change in pressure between a beginning and an end of a corresponding time period of the plurality of time periods.

13. The system of claim 12, wherein an offset between the consecutive time periods is less than a duration between the beginning and the end of each time period.

14. The system of claim 1, wherein the processor is configured to:
select a first time period comprising a first beginning time and a first ending time;
select a first pressure measurement of the proximal pressure measurements or the distal pressure measurements corresponding to the first beginning time and a second pressure measurement of the proximal pressure measurements or the distal pressure measurements corresponding to the first ending time;
calculate a first slope of the plurality of slopes for a first time period comprising a first beginning time and a first ending time;
select a second time period comprising a second beginning time and a second ending time, wherein the first time period partially overlaps with the second time period, and wherein the first beginning time is different from the second beginning time, and wherein the first ending time is different from the second ending time;
select a third pressure measurement of the proximal pressure measurements or the distal pressure measurements corresponding to the second beginning time and a fourth pressure measurement of the proximal pressure measurements or the distal pressure measurements corresponding to the second ending time; and
calculate a second slope of the plurality of slopes for a second time period comprising a second beginning time and a second ending time.

15. The system of claim 1, wherein identifying the change in sign of the plurality of slopes comprises:
calculating a plurality of averaged slopes based on the plurality of slopes; and
identifying a change in sign of the plurality of averaged slopes.

16. The system of claim 1, wherein the processor is configured to:
obtain proximal pressure measurements for a plurality of cardiac cycles of the patient from the at least one pressure-sensing instrument while the at least one pressure-sensing instrument is positioned within the vessel at the position proximal of a stenosis of the vessel; and
obtain distal pressure measurements for the plurality of cardiac cycles of the patient from the at least one pressure-sensing instrument while the at least one pressure-sensing instrument is positioned within the vessel at the position distal of the stenosis of the vessel.

17. The system of claim 16, wherein the processor is further configured to calculate, for a different cardiac cycle of the plurality of cardiac cycles, a further plurality of slopes over multiple time periods of a further the different cardiac cycle, wherein the time periods of the further cardiac cycle have a different duration than the time periods of the cardiac cycle.

18. A method of evaluating a vessel of a patient, the method comprising:
receiving, at a processor in communication with at least one pressure-sensing instrument sized and shaped for introduction into a vessel of the patient, proximal pressure measurements for a cardiac cycle of the patient while the at least one pressure-sensing instrument is positioned within the vessel at a position proximal of a stenosis of the vessel;
receiving, at the processor, distal pressure measurements for the cardiac cycle of the patient while the at least one pressure-sensing instrument is positioned within the vessel at a position distal of the stenosis of the vessel;
calculating, for the cardiac cycle, a plurality of slopes of at least one of the proximal pressure measurements or the distal pressure measurements for a plurality of time periods within the cardiac cycle, each slope of the plurality of slopes corresponding to a time period of the plurality of time periods, wherein consecutive time periods of the plurality of time periods partially overlap within the cardiac cycle;
selecting, using the processor, a diagnostic window within the cardiac cycle of the patient by identifying a change in sign of the plurality of slopes, wherein the diagnostic window encompasses only a portion of the cardiac cycle of the patient;
calculating, using the processor, a pressure ratio between the distal pressure measurements obtained during the diagnostic window and the proximal pressure measurements obtained during the diagnostic window; and
outputting, using the processor, the calculated pressure ratio to a display device in communication with the processor.

\* \* \* \* \*